US00PP11554P

United States Patent [19]

Sjulin et al.

[11] Patent Number: Plant 11,554

[45] Date of Patent: Oct. 10, 2000

[54] STRAWBERRY PLANT NAMED 'ALTA VISTA'

[75] Inventors: Thomas M. Sjulin, Aromas; Bruce D. Mowrey, La Selva Beach; Amado Q. Amorao, Camarillo; JoAnne F. Coss, Salinas; Kiyoshi Nishimori, Santa Maria, all of Calif.; Kristie L. Gilford, Dover, Fla.

[73] Assignee: Driscoll Strawberry Associates, Inc., Watsonville, Calif.

[21] Appl. No.: 08/858,424

[22] Filed: May 19, 1997

[51] Int. Cl.[7] ..... A01H 5/00

[52] U.S. Cl. ..... Plt./209

[58] Field of Search ..... Plt./48, 49, 208, Plt./209

[56] References Cited

U.S. PATENT DOCUMENTS

P.P. 6,579 1/1989 Bringhurst et al. ..... Plt./49

P.P. 7,615 8/1991 Bringhurst et al. ..... Plt./49

P.P. 8,661 3/1994 Bringhurst et al. ..... Plt./49

*Primary Examiner*—Howard J. Locker

*Attorney, Agent, or Firm*—Pennie & Edmonds LLP

[57] ABSTRACT

This invention relates to a new and distinct variety of strawberry plant named 'Alta Vista', botanically identified as *Fragraia×ananassa* Duch. The closest known variety is 'Key Largo'. The new variety is fully everbearing. The new variety is distinguished from 'Key Largo' by its medium to strong interveinal leaf-blistering, flat profile of the terminal leaflet, rounded basal shape of the terminal leaflet, rounded teeth on the terminal leaflet, medium in density petiole pubescence, outward pose of petiole hairs, medium anthocyanin coloration of the stolons in the fall of the year, an inflorescence relative position level with to above the leaves, broader than long petal length-to-width ratio, light red fruit flesh color, and early season of initial harvest.

3 Drawing Sheets

BACKGROUND OF THE INVENTION

The new variety of strawberry plant was selected as a seedling in a controlled breeding plot at a ranch in Santa Barbara County, Calif., U.S.A., on or about April 1993. The new variety originated as a result of a controlled cross between 'Key Largo', U.S. Plant Pat. No. 8,649, and the Driscoll Strawberry Associate, Inc. variety named 'L2' in an on-going breeding program. The seedling of the new variety was grown and asexually propagated by stolons at the nursery of Driscoll Strawberry Associates, Inc., in Shasta County, Calif. The new variety was further asexually propagated and extensively tested. This propagation and testing has demonstrated that the combination of traits disclosed herein which characterize the new variety are fixed and retained true to type through successive generations of asexual reproduction.

SUMMARY OF THE INVENTION

The present invention relates to a new and distinct strawberry variety. The varietal denomination of the new variety is 'Alta Vista' (formerly known as 'DX-4'). The variety is botanically identified at *Fragaria×ananassa* Duch. Among the characteristics which distinguish the new variety from other varieties of which we are aware are a combination of traits which include interveinal leaf-blistering, the profile of the terminal leaflet, the basal shape of the terminal leaflet, the shape of the teeth on the terminal leaflet, petiole pubescence, pose of petiole hairs, anthocyanin coloration of the stolons in the fall, inflorescence position relative to the leaves, petal length-to-width ratio, fruit flesh color, season of initial harvest and fruit bearing.

COMPARISON TO CLOSEST VARIETIES

The variety which we believe to be closest to 'Alta Vista' from those known to us is 'Key Largo' (U.S. Plant Pat. No.

8,649). The comparison descriptions are in accordance with UPOV terminology. There are several characteristics of the new variety that are different from, or not possessed by 'Key Largo'. For example, the average height of a plant of 'Alta Vista' is 22.00 cm, while that of 'Key Largo' is 23.15 cm. The average spread of a plant of 'Alta Vista' is 44.00 cm, while that of 'Key Largo' is 41.70 cm. The average number of crowns of 'Alta Vista' is 4.13, while that of 'Key Largo' is 2.70 cm. The interveinal blistering of the leaves of 'Alta Vista' is medium to strong, while that of 'Key Largo' is Weak or medium. The profile of the terminal leaflet leaf margin of 'Alta Vista' is flat, while that of 'Key Largo' is revolute. The basal shape of the terminal leaflet of 'Alta Vista' is rounded, while it is obtuse on 'Key Largo'. The average terminal leaflet width of 'Alta Vista' is 7.74 cm, while that of 'Key Largo' is 6.89 cm. The average terminal leaflet length of 'Alta Vista' is 8.14 cm, while that of 'Key Largo' is 7.09 cm. The length/width ratio of the terminal leaflet of 'Alta Vista' is 1.05 while that of 'Key Largo' is 1.03 . The teeth on the terminal leaflet of 'Alta Vista' are rounded, while those of 'Key Largo' are obtuse. The average tooth length of 'Alta Vista' is 6.40 mm, while that of 'Key Largo' is 6.50 mm. The average number of teeth per terminal leaflet of 'Alta Vista' is 21.93, while that of 'Key Largo' is 19.73.

The petiole pubescence of 'Alta Vista' is of medium density, while that of 'Key Largo' is sparse. The pose of the petiole hairs of 'Alta Vista' is outward, while that of 'Key Largo' is upward. The average petiole length of 'Alta Vista' is 16.81 cm, while that of 'Key Largo' is 18.45 cm. The Munsell color rating for petiole color of 'Alta Vista' is 3.7GY6.0/10.7, while that of 'Key Largo' is 3.7GY6.7/12.2. The anthocyanin coloration of the stolons in the fall of the year is medium on 'Alta Vista' and strong on 'Key Largo'. The inflorescence position relative to the leaves is level to above for 'Alta Vista' and level to below for 'Key Largo'. The average bract frequency of 'Alta Vista' is 0.13, while that of 'Key Largo' is 0.10. The average stipule length of 'Alta Vista' is 3.43 cm, while that of 'Key Largo' is 3.86 cm. The average stipule width of 'Alta Vista' is 9.10 mm, while that of 'Key Largo' is 9.20 mm. The stipule shape of 'Alta Vista' and that of 'Key Largo' are both laceolate. The Munsell color rating for stipule color of 'Alta Vista' is 4.1GY7.4/13.2, while that of 'Key Largo' is 4.3GY7.8/12.9. The stipule pubsecence of 'Alta Vista' is medium, while that of 'Key Largo' is light.

The petal length to width ratio of 'Alta Vista' is broader than long (0.98), while that of 'Key Largo' is as long as broad (1.02). Specifically, the average petal length of 'Alta Vista' is 12.70 mm, while that of 'Key Largo' is 12.20 mm. The average petal width of 'Alta Vista' is 13.00 mm, while that of 'Key Largo' is 12.00 mm. The average flower diameter of 'Alta Vista' is 32.70 mm, while that of 'Key Largo' is 32.50 mm. The average calyx diameter of 'Alta Vista' is 34.10 mm, while that of 'Key Largo' is 34.70 mm. The average sepal length of 'Alta Vista' is 10.40 mm, while that of 'Key Largo' is 12.44 mm.

The average fruit length of 'Alta Vista' is 4.58 cm, while that of 'Key Largo' is 3.41 cm. The average fruit width of 'Alta Vista' is 4.23 cm, while that of 'Key Largo' is 3.52 cm. The fruit length/width ratio is 1.08 for 'Alta Vista' and 0.97 for 'Key Largo'. The fruit flesh color of 'Alta Vista' fruit is light red, while that of 'Key Largo' is medium red. Specifically, the Munsell color rating for fruit neck color of 'Alta Vista' is 5.9R3.6/15.2, while that of 'Key Largo' is 5.5R2.9/11.6. The Munsell color rating for fruit body color of 'Alta Vista' is 6.0R/3.1/12.0, while that of 'Key Largo' is 5.5R2.9/11.6. The Munsell color rating for achene coloration of 'Alta Vista' is 6.3R/2.5/8.9 on the sun side ofthe berry and 5.7Y7.3/12.7 on the shade side, while those of 'Key Largo' are 6.0R/3.1/12.0 and 5.6Y7.9/13.9, respectively.

The season of harvest is early for 'Alta Vista', while that of 'Key Largo' is early to mid-season. Lastly, 'Alta Vista' is fully everbearing, while 'Key Largo' is partially everbearing. As to tendency to form runners, 'Alta Vista' has little tendency to form runners in the fruiting field following supplemental cold storage, averaging 0.06 runners/plant. This is similar to Commander (U.S. Plant Pat. No. 7,024) (0.05 runners/plant) and less than 'Key Largo' (0.48 runners/plant). As to chilling requirements, 'Alta Vista' requires approximately 4 to 6 weeks of supplemental cold storage before planting. This is higher than 'Key Largo' and similar to other everbearing or day-neutral varieties such as 'Seascape' (U.S. Plant. Pat. No. 7,614) and 'Selva' (U.S. Plant Pat. No. 5,266).

Regarding isozyme analysis, the phosphoglucoisomerase (PGI) isozyme banding pattern for 'Alta Vista' and 'Key Largo' is A1. The leucine aminopeptidase (LAP) isozyme banding pattern for 'Alta Vista' and 'Key Largo' is B3. The phosphoglucomutase (PGM) isozyme banding pattern for 'Alta Vista' is C2 while that for 'Key Largo' is C4. See *J. Amer. Soc. Hort. Sci.* 106:684 (1981).

TABLE 1

Isozyme Phenotypes for 'Alta Vista' and 'Key Largo'

| | Cultivar | |
|---|---|---|
| Locus | 'Alta Vista' | 'Key |
| Largo' | | |
| PGI | A1 | A1 |

TABLE 1-continued

Isozyme Phenotypes for 'Alta Vista' and 'Key Largo'

| | Cultivar | |
|---|---|---|
| Locus | 'Alta Vista' | 'Key |
| LAP | B3 | B3 |
| PGM | C2 | C4 |

The 'Key Largo' isozyme data is from U.S. Plant Pat. No. 8,649.

BRIEF DESCRIPTION OF THE ILLUSTRATIONS

The accompanying photographs show typical specimens of the new variety, including fruit, foliage and flowers, in color as nearly true as it is reasonably possible to make in color illustrations of these characteristics.

DESCRIPTION OF THE NEW VARIETY

Figure 1:
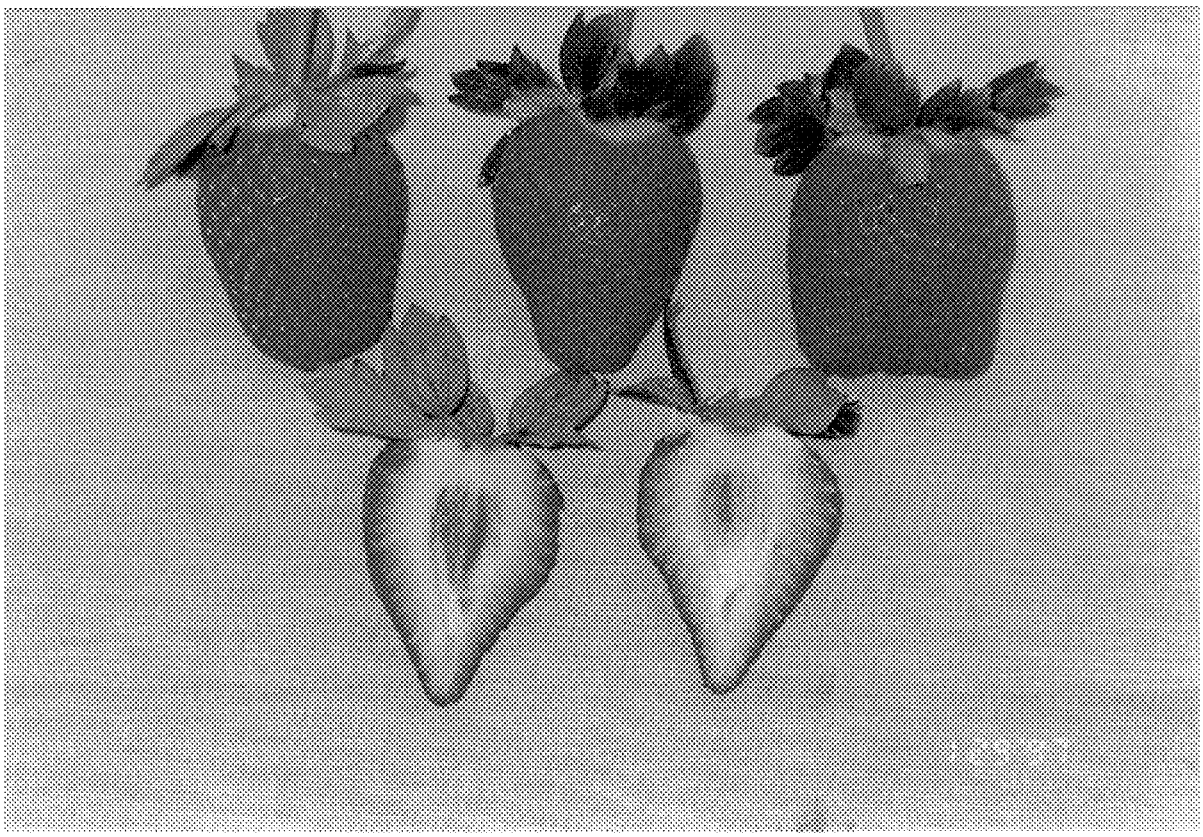
FIG. 1 shows typical whole fruit and the fruit in longitudinal section, illustrating the typical flesh and flesh coloration, core and shape of the new variety.
Figure 2:
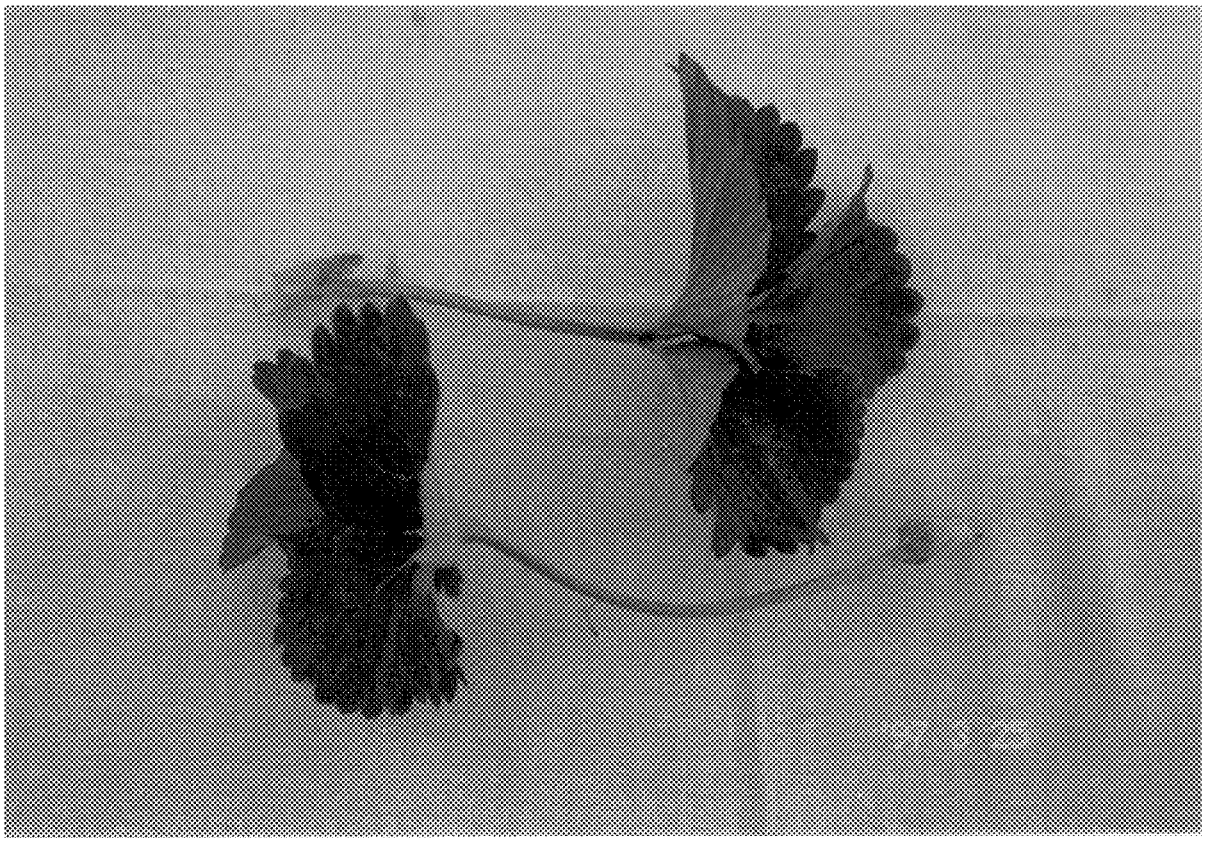
FIG. 2 shows the upper surface of two typical folioles of the new variety.
Figure 3:
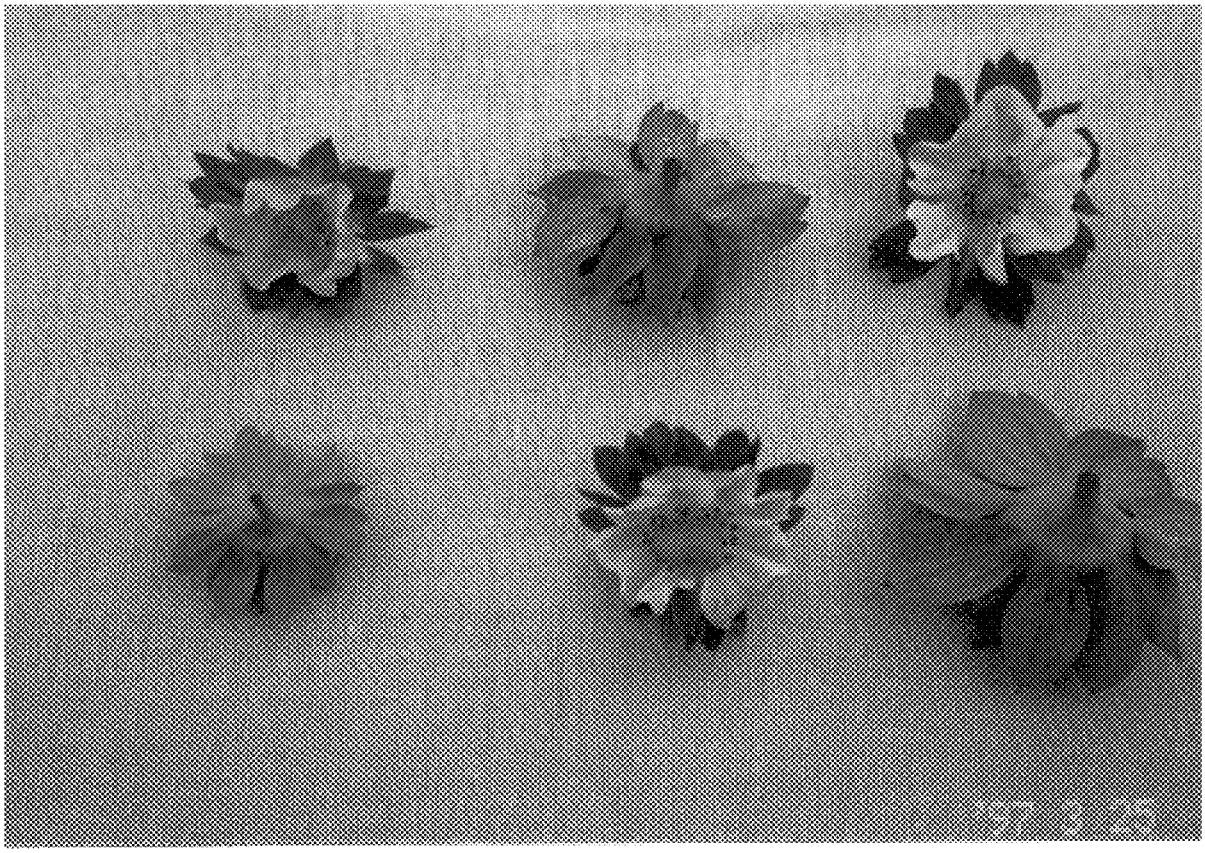
FIG. 3 shows the flowers and reproductive organs of the new variety, as well as the size and position of the petals and sepals.

The following detailed description of the new variety is based upon observations taken of plants and fruit grown in experimental test plots in 1997 at Garrison Farm in Hillsborough County, Fla., U.S.A. The plant material was planted on Oct. 9, 1996, and 'Alta Vista' was grown in a forcing system during the winter. Observations of 'Alta Vista' and 'Key Largo' were taken in a side-by-side comparison in January 1997. Additional measurements were taken on the ranch of Driscoll Strawberry Associates, Inc. in Monterey County, Calif. in the summer of 1998. This description is in accordance with UPOV terminology. Color designations, color descriptions, and other phenotypical descriptions may deviate from the stated values and descritions depending upon variation in environmental, seasonal, climatic and cultural conditions. Colors are described using standard Munsell Notation.

Propagation

The new variety is principally propagated by way of stolons. Although propagation by stolons is presently preferred, other known methods of propagating strawberry plants may be employed. As to regional adaptation, 'Alta Vista' is best adapted to a Winter plant system in the area of Watsonville and Salinas, Calif. It also can be grown in Florida for production of fruit in the winter months.

Characteristics of the New Variety

The following information is provided to describe the new variety.

Plant: The plants are of open to medium density with flat globose habit and weak to medium vigor. The average height of a plant of 'Alta Vista' is 22.00 cm. The average spread of a plant of 'Alta Vista' is 44.00 cm. The plant of 'Alta Vista' is typically smaller and more compact when grown in Florida during the winter months than when grown in northern California. The average number of crowns of 'Alta Vista' is 4.13. As to the comparative productivity, 'Alta Vista' is highly productive producing 2052 g of marketable fruit per plant on average in northern California in 1997, compared to 'Key Largo' which produced 1272 g of marketable fruit per plant on average. The length of the production season of 'Alta Vista' was from the week ending Apr. 12, 1997 through the week ending Nov. 1, 1997 in Watsonville, Calif. and from the week ending Dec. 7, 1996 through the week ending Apr. 15, 1997 in Dover, Fla. The length of the production season for 'Key Largo' was from the week ending Apr. 12, 1997 through the week ending Nov. 1, 1997 in Watsonville, Calif. and from the week ending Dec. 14, 1996 through the week ending Apr. 15, 1997 in Dover, Fla.

Leaves: The upperside of the leaves are medium to dark green with a Munsell color rating of 8.9GY2.3/4.7. The color of the underside of the leaves is gray-green which is not referenced on the Munsell Color Chart.

The leaf profile is strongly concave and there is medium to strong interveinal leaf-blistering. Plants have three leaflets only. The terminal leaflet margin profile is flat and the length-to-width ratio of the terminal leaflet is broader than long. The shape of the base of the terminal leaflet is rounded and the teeth of the terminal leaflet are rounded. The average terminal leaflet width of 'Alta Vista' is 7.74 cm. The average number of teeth on the terminal leaflet of 'Alta Vista' is 21.93. The average length of the teeth on the terminal leaflet for 'Alta Vista' is 6.40 mm.

The petiole pubescence is of medium density and the pose of the petiole hairs is outwards. The average petiole length of 'Alta Vista' is 16.81 cm. The Munsell color rating for petiole color of 'Alta Vista' is 3.7GY/6.0/10.7. The average stipule length of 'Alta Vista' is 3.43 cm. The average stipule width of 'Alta Vista' is 9.10 mm. The stipule shape of 'Alta Vista' is lanceolate. The Munsell color rating for stipule color of 'Alta Vista' is 4.1GY7.4/13.2. The stipule pubescence of 'Alta Vista' is medium.

Stolons: 'Alta Vista' has few to a medium number of stolons of medium thickness with medium anthocyanin coloration and medium pubescence.

Inflorescence: The position of the inflorescence is from level with to above the foliage. The flowers are large in size. The average petal length of 'Alta Vista' is 12.70 mm. The average petal width of 'Alta Vista' is 13.00 mm. The average flower diameter of 'Alta Vista' is 32.70 mm. The average calyx diameter of 'Alta Vista' is 34.10 mm. The average sepal length of 'Alta Vista' is 10.40 mm.

The diameter of the calyx is larger than the corolla. On secondary flowers, the diameter of the inner calyx is smaller than the outer calyx. On secondary flowers with 5 to 6 petals, the petals are very overlapping. The petal length-to-width ratio on secondary flowers is broader than are long (0.98).

The fruiting trusses are long in length and the attitude at first picking is prostrate.

Fruit: Observations of the fruit were taken of secondary fruit on one year old plants. The fruit are predominantly conical in shape. The fruit ratio of length to maximum width are longer than broad. The fruit are large in size. There is a marked difference in fruit shape between the primary and secondary fruits. The band without achenes is narrow. The fruit surface has a weak unevenness. Primary berries tend to be cylindrical to wedge shaped, while secondary fruit are more conical to almost cylindrical.

Fruit Color: The fruit skin color is a slightly uneven red with a Munsell color rating of 6.0R 3.1/12.0 and strong glossiness. The Munsell color rating for fruit neck is 5.9R3.6/15.2, and that for fruit body is 6.0R3.1/12.0.

The insertion of the achenes is from the level with the surface to above the surface of the fruit. The Munsell color rating for achene coloration on the sun side of the berry is 6.3R/2.5/8.9 and that on the shade side is 5.7Y/7.3/12.7.

The calyx is inserted level with the fruit and the pose of the calyx segments is reflexed. The calyx diameter is very much larger than the fruit diameter. The adherence of the calyx to the fruit is strong.

The fruit flesh has a medium to firm firmness when fully ripe. The color of the fruit flesh is light red with a Munsell color rating of 5.1R 4.1/16.1 and white. The fruit flesh color is uneven.

The fruit has a strong sweetness, with medium acidity and very fine to fine texture. The soluble solids content of the fruit of 'Alta Vista' measured in percent Brix averaged 9.99 for the 1998 harvest season. The percent Brix content is an indirect measure of the sugar content or sweetness.

Chilling requirements: 'Alta Vista' requires approximately 4 to 6 weeks of supplemental cold storage before planting.

Tendency to form runners: 'Alta Vista' has little tendency to form runners in the fruiting field following supplemental cold storage, averaging 0.06 runners/plant.

The time of flowering when 50% of the plants are at first flower is early. When the 'Alta Vista' variety was planted in Florida in eary October, the plants began flowering in early November.

Length of Season of Production: The length of the production season of 'Alta Vista' in Watsonville, Calif. was from the week ending Apr. 12, 1997 through the week ending Nov. 1, 1997 and in Florida it was from the week ending Dec. 7, 1996 through the week ending Apr. 15, 1997.

The harvest maturity when 50% of the plants possess ripe fruit is early. For 'Alta Vista' planted in Florida in early October, 50% of the plants possessed ripe fruit in early December. 'Alta Vista' has moderate shelf life and shipability. Shelf life of 'Alta Vista' is poorer than 'Key Largo' and similar to the variety 'Swede' (U.S. Plant Pat. No. 6,191).

'Alta Vista' is a fully everbearing variety. Everbearing strawberrry varieties are characterized as plants which fruit two or more times per season, and the summer flowering is governed by long photoperiods. See *Advances in Fruit Breeding*, page 86 (eds. Jules Janick and James N. Moore, 1975).

Resistance to Stress

The new variety 'Alta Vista' is moderately resistant to high temperatures. 'Alta Vista' is resistant to high pH.

Disease Resistance and Susceptibility

The 'Alta Vista' fruit is moderately susceptible to decay by Botrytis fruit rot. 'Alta Vista' is moderately resistant to powdery mildew and leaf spots (*Xanthomonus fragariae*).

The 'Alta Vista' variety is susceptible to injury by *Tarsonemus pallidus, Aphelencoides fragariae,* Aphis spp., and lygus bus (*Lygus hesparus*).

What is claimed is:

1. A new and distinct variety of strawberry plant, substantially as shown and described.

* * * * *